US010039614B2

(12) United States Patent
Bassion, Sr. et al.

(10) Patent No.: US 10,039,614 B2
(45) Date of Patent: Aug. 7, 2018

(54) MEDICAL DEVICE TRACKING AND REPROCESSING SYSTEM

(71) Applicants: David Bassion, Sr., Philadelphia, PA (US); David Bassion, Jr., Philadelphia, PA (US); Donald R. Moyer, Telford, PA (US)

(72) Inventors: David Bassion, Sr., Philadelphia, PA (US); David Bassion, Jr., Philadelphia, PA (US); Donald R. Moyer, Telford, PA (US)

(73) Assignees: David Bassion, Sr., Philadelphia, PA (US); David Bassion, Jr., Philadelphia, PA (US); Donald R. Moyer, Telford, PA (US)

(*) Notice: Subject to any disclaimer, the term of this patent is extended or adjusted under 35 U.S.C. 154(b) by 0 days.

(21) Appl. No.: 15/470,710

(22) Filed: Mar. 27, 2017

(65) Prior Publication Data

US 2017/0277864 A1    Sep. 28, 2017

Related U.S. Application Data

(60) Provisional application No. 62/313,386, filed on Mar. 25, 2016.

(51) Int. Cl.
*G06F 19/00* (2018.01)
*A61B 90/90* (2016.01)
(Continued)

(52) U.S. Cl.
CPC .............. *A61B 90/90* (2016.02); *A61B 90/70* (2016.02); *A61B 90/98* (2016.02); *G06Q 10/087* (2013.01);
(Continued)

(58) Field of Classification Search
None
See application file for complete search history.

(56) References Cited

U.S. PATENT DOCUMENTS 8,242,907 B2 *   8/2012   Butler ................. G06K 7/0008
                                                340/10.1
8,266,129 B2 *   9/2012   Shimizu ............. A61B 1/00059
                                                134/3
9,361,530 B2 *   6/2016   Sly ..................... G06K 9/00892

FOREIGN PATENT DOCUMENTS

EP      1725161 B1    1/2010
JP      5562455 B2    6/2001
(Continued)

*Primary Examiner* — K. Wong
(74) *Attorney, Agent, or Firm* — Gearhart Law LLC (57) ABSTRACT

The system describes a software implementation to track use and cleaning of medical devices in hospitals and other medical settings. Further, the system may track cleaning (e.g. temperature, movement) and location (e.g. RSSI, etc.) of a medical device. The system may include boxes that sit on the wall in the cleaning rooms, sensors on the medical devices, sensors on the individuals who handle the devices, and a separate Wi-Fi® wireless network that relays information from the box to a computer in the facility, that relays the information back to the cloud. In some embodiments, a supervisor or other superior gets notified if proper cleaning and reprocessing methods are not used. In other embodiments, the surgeon/doctor can scan a medical device when presented for use and see its use and cleaning history.

15 Claims, 10 Drawing Sheets

(51) Int. Cl.
*A61B 90/70* (2016.01)
*A61B 90/98* (2016.01)
*G06Q 10/08* (2012.01)
*G06Q 50/22* (2018.01)
*G16H 10/40* (2018.01)

(52) U.S. Cl.
CPC ............ *G06Q 50/22* (2013.01); *G16H 10/40* (2018.01); *A61B 2090/701* (2016.02)

(56) References Cited

FOREIGN PATENT DOCUMENTS

| WO | 2012085791 A1 | 6/2012 |
| WO | 2015034824 A1 | 3/2015 |

* cited by examiner

MEDICAL DEVICE TRACKING AND REPROCESSING SYSTEM

CLAIM OF PRIORITY

This application claims the priority of U.S. Ser. No. 62/313,386 filed on Mar. 25, 2016, the contents of which are fully incorporated herein by reference.

FIELD OF THE EMBODIMENTS

The field of the embodiments of the present invention relate to systems and method to track the use and sanitation of medical devices. In particular, the present invention and its embodiments pertain to a software system that tracks at least movement and temperature associated with the use and cleaning of medical devices.

BACKGROUND OF THE EMBODIMENTS

Many medical devices in the medical community are controlled by software implementations and are capable of transmitting data via a communication network. Modern computer and communications technologies provide the ability to network systems together and interface directly with medical facility computer systems.

Endoscopes, one type of medical device, comprise protectively encased bundles of flexible optical fibers used to transmit images to the operator at one end from otherwise inaccessible regions into which the opposite end of the instrument is inserted, so as to obtain a view of the structures surrounding such regions. Such an arrangement makes the visual examination, and even photographing, of structures inside the human body possible.

Not only can an endoscope be inserted into the region of interest and manipulated to permit viewing in different directions, but also such instruments are typically built to include means that allow the insertion of fluids into the region of interest. Often, there are also means for the removal of tissue from portions of the surrounding organ structures. Thus, in addition to the fiber optic bundle, there is usually provided a plurality of enclosed channels or passageways more or less paralleling the direction of the fiber optic bundle.

As a result of the desired utilizations, endoscopes are complex, highly instrumented medical devices that are simply too costly to be disposable. Therefore, it is desirable to reuse such devices. However, endoscopes are exposed to bodily fluids and tissue, both internally and externally making it necessary to clean and sanitize these devices thoroughly before they can be reused. The sterilization process is relatively long, and may take many days until an endoscope can return to use.

Thus, it is critical to have an invention that enables proper cleaning parameters as well as monitoring location and usage to ensure all proper protocols are performed. For example, in use with an endoscope, the monitoring system would insure that the correct steps were performed to disinfect, clean, sanitize, and rinse the endoscope as well as provide for data associated with such usage and its movements (location). The present invention has applicability to medical products beyond endoscopes. It could be used for any software controlled system that controls critical steps or processes in relation to a medical device.

Review of related technology:

U.S. Pat. No. 5,882,589 pertains to a device for cleaning, disinfecting, and/or drying an endoscope consists of a basin supported on a base. The basin forms a channel that defines a teardrop shape. The device includes a lid that sealingly engages the basin. During operation, the endoscope to be cleaned is completely immersed in cleaning solution in the basin. The basin includes injectors arranged so as to create a rotating flow of cleaning liquid and sterile rinsing water or recycled drying air within the channel. The vessel also includes injection nozzles that attach to various inlets of the endoscope to inject products at specified pressures and to continuously test the tightness of the seal.

U.S. Patent Application 2014/0270375 pertains to a motion tracking system monitors the motions performed by a user based on motion data received from one or more sensors. The motion tracking system may include a motion tracking device with one or more sensors, a smart device with one or more sensors and/or a server. As the user interacts with the motion tracking system or smart device the motion data generated by one or more sensors is processed by a software application. The software application generates interpreted data based on the motion data and contextual data such as the equipment being used by the user. Feedback is then provided to the user during and/or after the user has performed a motion or a set of motions. The feedback provided to the user may be visual, audio or tactile. The application may be used to monitor a routine in a sporting, fitness, industrial or medical environment, for example.

European Patent 1,725,161 pertains to an on board monitor for an endoscope reprocessor for monitoring the performance and order of a predetermined set of critical steps for reprocessing an endoscope. The monitor will only allow the overall system to reach the last step indicating successful completion of the process related to the critical steps representing successful reprocessing of an endoscope after the system successfully completes all of the previous critical steps and in the correct order.

French Patent 2,914,554 pertains to a method involving recording date and information of disinfection and utilization of a medical apparatus i.e. probe, based on identification information of the apparatus. The information of disinfection and utilization are sequenced on a patient based on the identification information. An authorization or interdiction instruction of the utilization of the apparatus is developed from the sequencing. The utilization is authorized, if the disinfection adapted to the utilization is in place, and the utilization is interdicted, if the disinfection adapted to the utilization is not in place.

Various devices and methodologies are known in the art. However, their structure and means of operation are substantially different from the present disclosure. The other inventions also fail to solve all the problems taught by the present disclosure. At least one embodiment of this invention is presented in the drawings below and will be described in more detail herein.

SUMMARY OF THE EMBODIMENTS

The present invention teaches a medical device cleaning and tracking system comprising: a processor having a memory, the memory having computer readable instructions stored thereon that when executed by the processor, enable monitoring of at least one medical device having a first tag, wherein the first tag is configured to measure at least location, movement, and temperature of the at least one medical device; a second tag operably coupled to the processor, the second tag being configured to monitor the at least one medical device, wherein the second tag is configured to communicate with the first tag and receive information pertaining to the at least one medical device therefrom. The system further comprising at least one additional tag configured to monitor the at least one medical device, wherein the at least one medical device is an endoscope.

A method of tracking a medical device, the method comprising the steps of: monitoring, via a processor, a location of at least one medical device; monitoring, via the processor, a temperature of the at least one medical device; monitoring, via the processor, a movement of the at least one medical device; logging, via the processor, the location, the temperature, and the movement of the at least one medical device; storing, on a computer readable memory operably coupled to the processor, the location, the temperature, and the movement of at least one medical device; wherein if a location, temperature, or movement of the at least one medical device meets a predetermined threshold, then no alert is generated; and wherein if a location, temperature, or movement of the at least one medical device does not meet a predetermined threshold, then an alert is sent to at least one electronic device. The method further comprises at least one additional tag configured to monitor the at least one medical device, wherein the at least one medical device is an endoscope.

The present invention describes and teaches a system and software to track use and cleaning of endoscopes and other medical devices in hospitals and patient treatment/care settings. In some embodiments, the system includes boxes that sit on the wall in the cleaning rooms, sensors on the endoscopes, sensors on the nurse/techs (each of whom is assigned a number), and a separate Wi-Fi® wireless network that relays information from the box to a computer in the facility, that relays the information back to the cloud. There, in some embodiments, are also web and/or mobile applications (apps) for the nursing supervisor and the surgeon/doctor and/or a secure website/portal to access the reports and data. The supervisor or other superior may get notified via the app if proper cleaning methods are not used. In turn, the surgeon/doctor can scan an endoscope when presented for use and see its use and cleaning history. In addition to the product, the system will also be in possession of a large body of data that is of value to not only the individual hospital customers, but also the endoscope providers. No private health information (PHI) is preferably collected on anyone.

The system, when implements, can comprise many form factors. For example, the box or computer may be a modified credit card-sized single-board computer. Further, the system may implement Bluetooth® wireless communication technology. In some embodiments, this comprises not merely relying on a Bluetooth® connection between the sensor and the box but rather the sensor broadcasting to the box to allow information to be captured.

In another embodiment, there are two boxes, for example, two credit card-sized single-board computers mounted on the walls in the cleaning room, a box in the storage closet and a box in the exam room (each of these may be "wall units"). The key purpose of these boxes is to transmit location constantly of the scopes. There is also a box mounted by each sink and one by each washer in the cleaning room (these may be "device units").

The tag or beacon on the endoscope or other medical device always broadcasts its location. Each box receives the location information, calculates an average of the location readings upon receiving a certain number of readings and sends that average to a local personal computer (PC) or server. When there are two or more boxes in a room of a given vicinity, the average location data of the two boxes is used. The lower the reading indicates where the scope is at a particular time. The PC takes all the readings for a given scope and calculates where the scope is every 30 seconds to 1 minute. It then sends that data to the cloud. Thus, the box is not just a pass through, but is processing data.

In some embodiments, if the PC determines that a scope is in the cleaning room, near the sink or washer, it tells the sink/washer to turn on additional readings to be broadcast. If the system is near the sink, which is supposed to be the first step, the device unit will tell the scope sensor to turn on and broadcast temperature and motion (accelerometer) readings. Then, when the system is near the sink, that device unit will tell the scope sensor to shut off the motion readings (however, if the sink was skipped, which it shouldn't be, it will also tell the scope to turn on the temperature reading).

When the scope is located in either the closet or the exam room, the wall unit will tell the scope sensor to turn off the temperature/motion readings if they are not already shut off.

In yet other embodiments, each part of the system (box, sensors, etc.) must be logged in to the system to be effective. Several spare boxes may be provided to a particular user or facility in case, the users need to switch them out. Each month, all the tags may be replaced. In such a scenario, a box with the new tags will be shipped to the hospital and each month the used tags and any used boxes will need to be returned. The boxes will be programmed to check for periodic software updates, which can be done remotely.

The cloud software collects all the data from the hospital, filters out any noise and detects the location of each device at each second. The cloud software then creates alerts as needed.

Yet in some other embodiments, the history (usage, location, cleaning, etc.) for a particular device can be viewed on demand. History also available for device units. A user can select reports from app and they will be emailed or otherwise presented to the user. There may be options for automatic daily summary reports that goes via email to appropriate managers.

In general, the present invention succeeds in conferring the following, and others not mentioned, benefits and objectives.

It is an object of the present invention to provide a medical device tracking system that ensures proper sanitation protocols are adhered.

It is an object of the present invention to provide a medical device tracking system that monitors a location of a medical device.

It is an object of the present invention to provide a medical device tracking system that monitors movement of a medical device.

It is an object of the present invention to provide a medical device tracking system that monitors temperature(s) of a medical device.

It is an object of the present invention to provide a medical device tracking system that is useful in connection with endoscopes.

It is an object of the present invention to provide a medical device tracking system that enables doctors/surgeons/physicians to view a usage history and reprocessing history of a given medical device.

It is an object of the present invention to provide a medical device tracking system that reduces the incidence of infection.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Generally, the present system refers to a software system capable of tracking use and cleaning of medical devices, particularly endoscopes, in medical settings. The system may include "boxes" that sit on the wall, floor, etc. of various rooms throughout the medical setting (e.g. hospital rooms). For example, a box may be present in the cleaning rooms, sinks, cleaners, closets, etc. Sensors or "tags" are operably coupled to the medical device and persons working in the medical setting. In some embodiments, there is a separate communications network (e.g. Wi-Fi® wireless communication network) that is configured to relay information from the box to another computer in the facility for storage and interpretation. The information may then also be stored, under encryption, in the cloud. The boxes described in the present invention are referred to as PD boxes or branded as The Observer.

Figure 1:
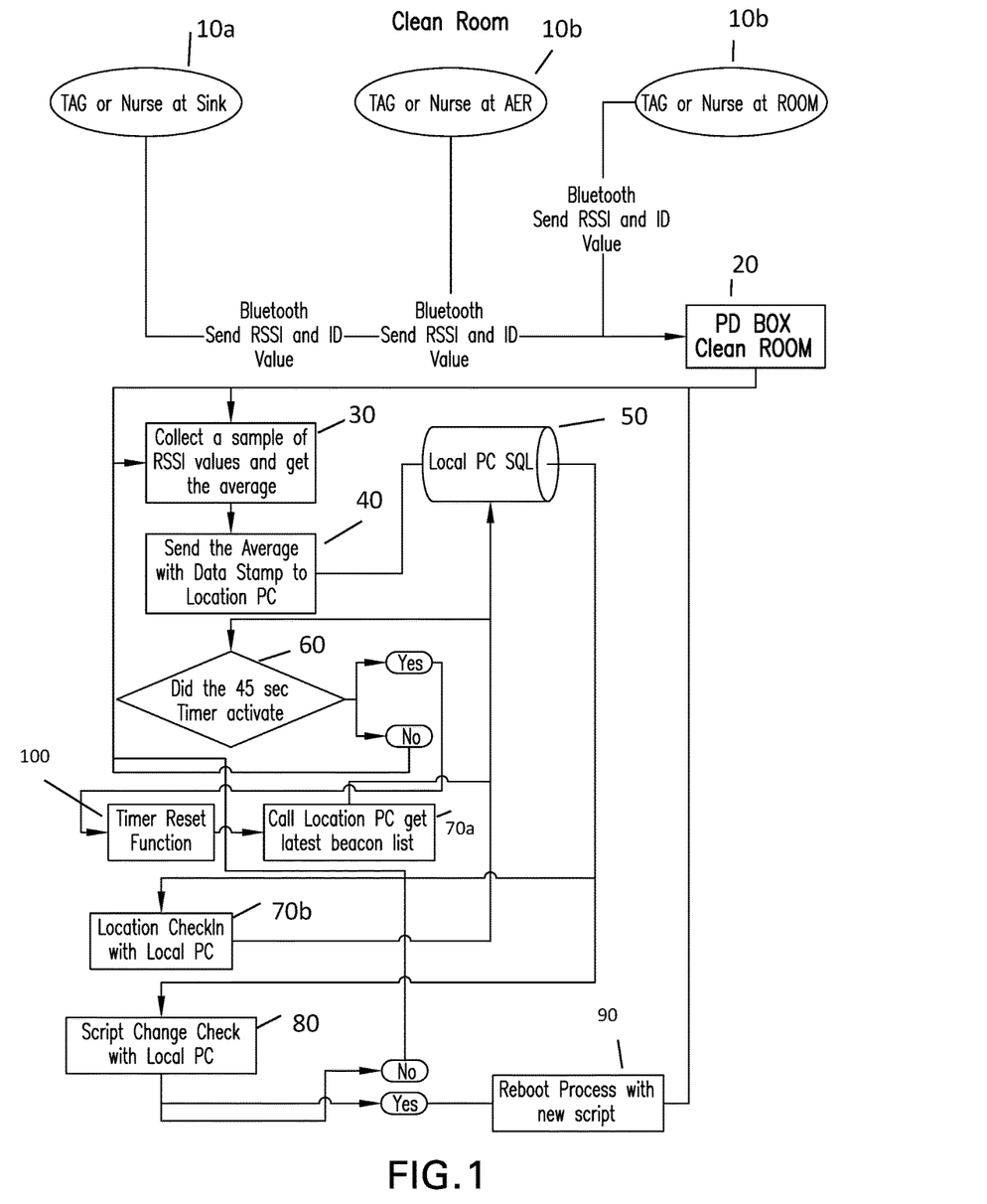
FIG. 1 is a flowchart illustrating an embodiment of the present system reading the tags in a clean room.

Referring now to FIG. 1, illustrating an embodiment of the present system reading the tags in a clean room. The tag coupled to the medical device is primarily intended to be broadcasting a signal such that the location of the medical device can be readily ascertained. In some embodiments, this is a continuous signal broadcast, whereas in other embodiments, the signal is sent intermittently. The boxes, positioned throughout the medical setting, are configured to receive information from the tags associated with the medical devices. Preferably, the boxes can read information on a tag when the tag is positioned from up to about 50 m away from the particular box's location. If more than two boxes are in the same vicinity an average of the location reading may be used to definitively pinpoint the location of the medical device. FIG. 1 describes the process flow of the clean room. The Scope Tag or Nurse Tag at the sink 10a, Automated endoscope reprocessors (herein AER) 10b, or Room 10c sends a Received Signal Strength Indicator (herein RSSI) and an identification (herein ID) Values over Bluetooth to the PD Box located in the Clean room, 20. The PD Box 20 located in the clean room then collects a sample of RSSI values 30 and gets the average per tag 40. The averages with data stamps are then sent to the personal computers (herein PC) at that location 50. Every 45 seconds 60, the PD box then sends a location check 70a, 70b in to the sequel database (herein SQL) and then collects the latest tag list from the SQL database. The PD box also sends a script change check 80 to the SQL and if needed, will update and reboot the process if there are any new changes to the scripts 90. In the event a new timing interval is created, a timer can resent this function with a new second or minute interval 100.

In a preferred embodiment, receive signal strength indication (RSSI) is used to determine the location of the medical device. The boxes can interpret the location signal emanating from the tag on the medical device thereby determining via the signal strength an approximate distance from the box. As noted above, the more boxes that are used in making the determination, the more precise the location will be.

Figure 2:
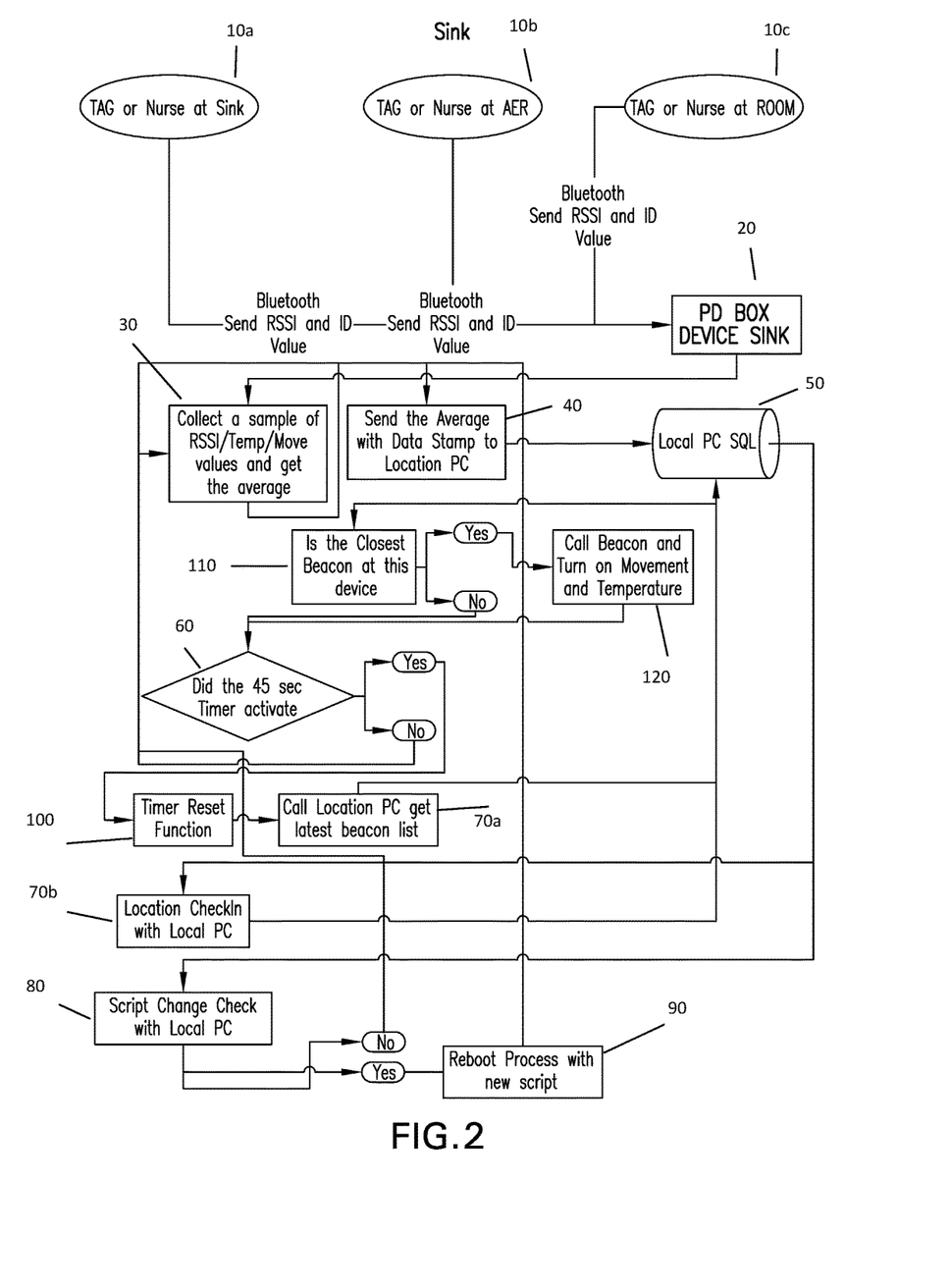
FIG. 2 is a flowchart illustrating an embodiment of the present system reading the tags near a sink.
Figure 3:
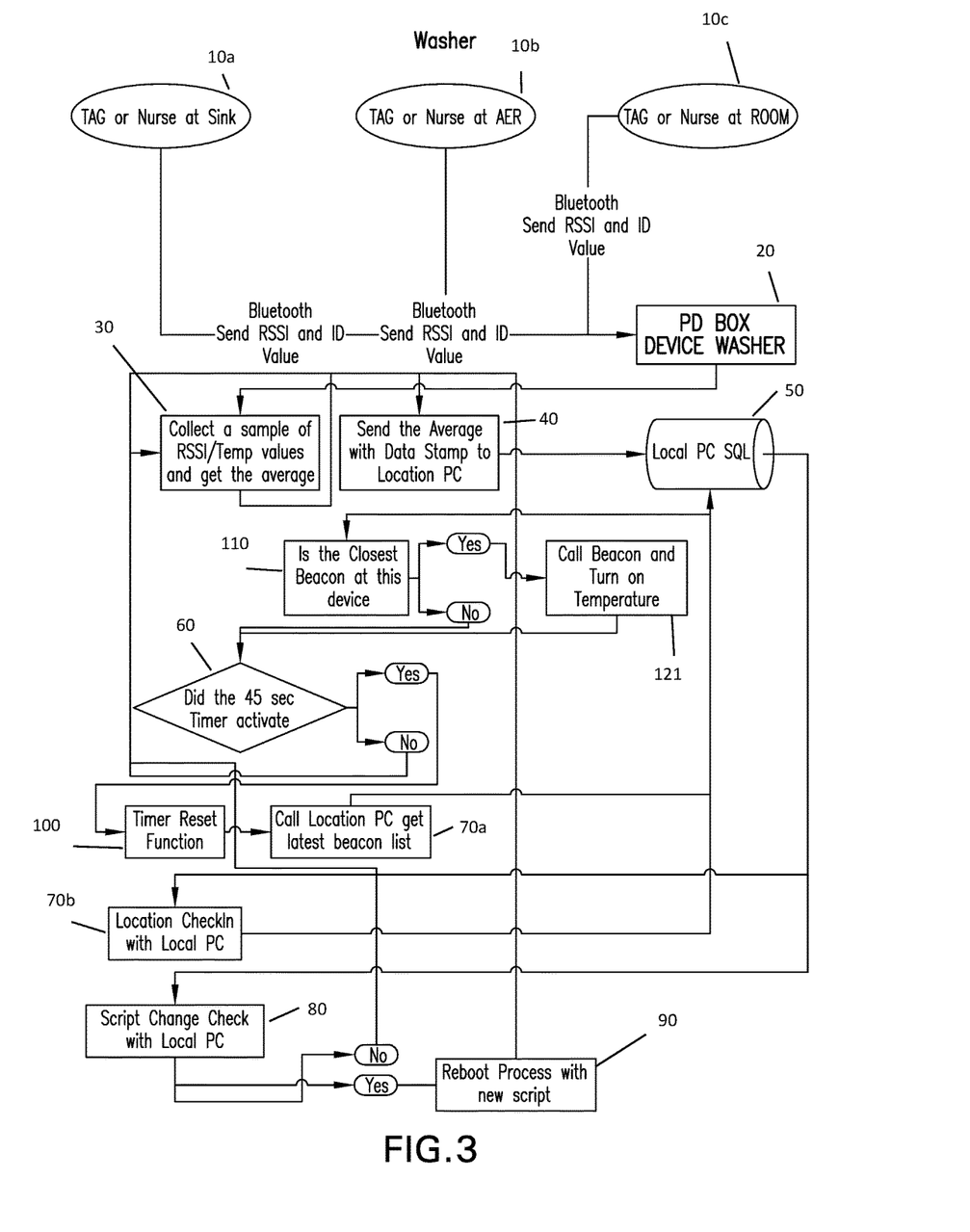
FIG. 3 is a flowchart illustrating an embodiment of the present system reading the tags near an automated endoscope reprocessor.
Figure 4:
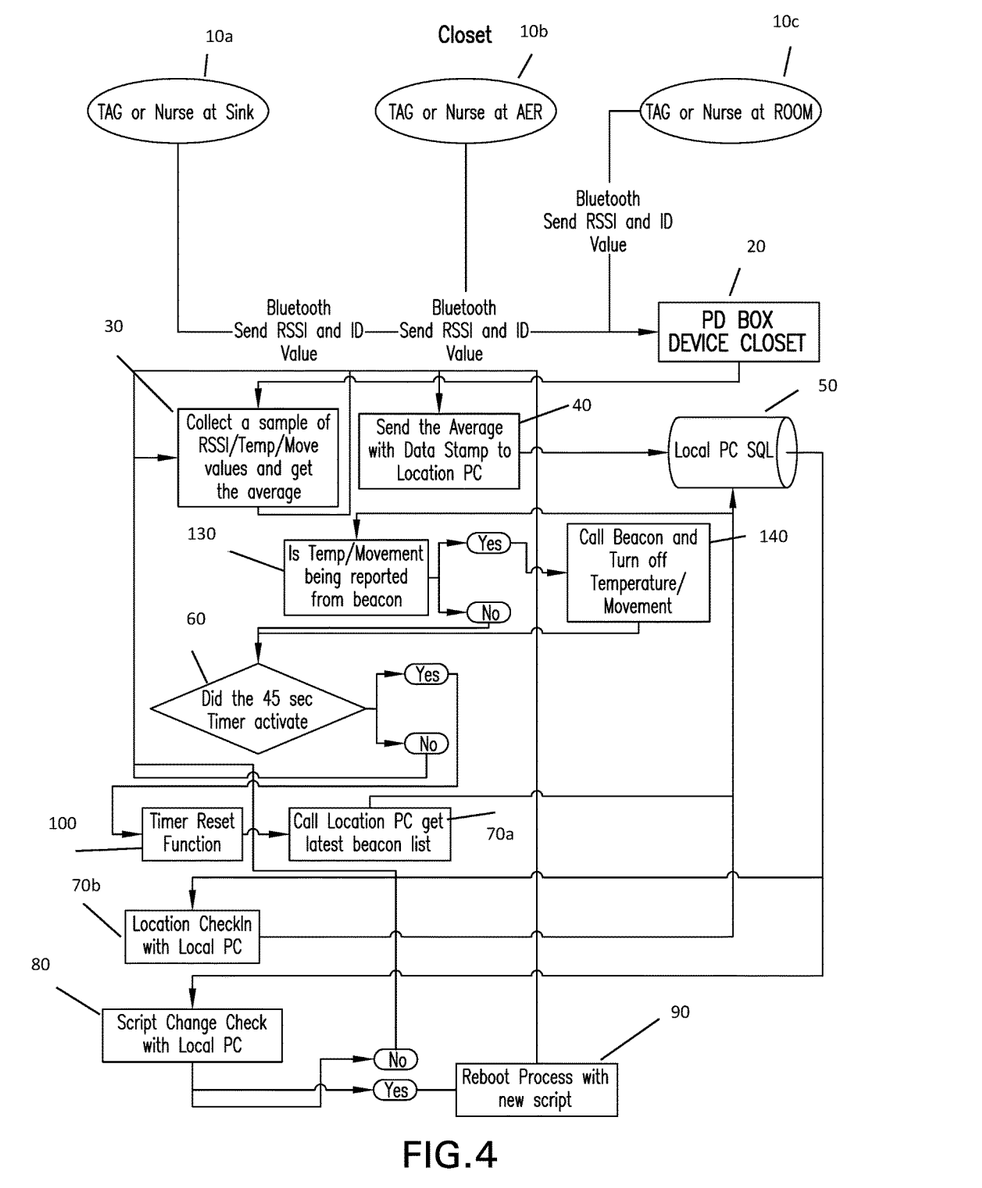
FIG. 4 is a flowchart illustrating an embodiment of the present system reading the tags in a closet.

FIGS. 2-4 are flowcharts illustrating a protocol for the system when the medical device is in the sink area, wash area, or the closet area respectively. If the processor (computer) determines that a medical device bearing a tag is in the cleaning room, near the sink or washer, it tells the sink/washer to turn on additional readings to be broadcast.

If near the sink, which is generally supposed to be the first step in the reprocessing of a medical device, the computer may tell the medical device tag to turn on and broadcast temperature and motion or movement readings. The temperature readings are preferably captured using a temperature sensor and the motion or movement readings are preferably captured using an accelerometer and/or gyroscope. Then, when near the sink, that box can tell the tag on the medical device to shut off the motion readings.

When the medical device is located in either the closet or the exam room, the box located in that room may tell the tag on the medical device to turn off the temperature/motion readings if they are not already shut off.

In FIG. 2, the sink process flow is described. In FIG. 2, the Scope Tag or Nurse Tag at the sink 10a, AER 10b, or Room 10c sends RSSI and ID Values over Bluetooth to the PD Box located above the sink. The PD sink box then collects a sample RSSI, Temperature, and movement values. It takes the average per tag of these values and with a date stamp, sends them to the PC's at that location. Every 45 seconds the PD box then sends a location check in to the SQL database and it then collects the latest tag list from the SQL database. The PD box also sends a script change check to the SQL database and if needed will update and reboot if there are any new changes to the scripts. The PD box determines from the data collected if the closest tag is at the sink PD box 120. If the tag is closest to the sink PD box, it will send a signal or call to the tag to turn on temperature and movement 120.

FIG. 3 describes the Washer process and method. In FIG. 3, the Scope Tag or Nurse Tag at the sink, AER, or Room sends RSSI and ID Values over Bluetooth to the PD Box located above the washer. The PD washer box then collects a sample RSSI and Temperature values. It takes the average per tag of these values and with a date stamp sends them to the PC at that location. Every 45 seconds the PD box then sends a location check in to the SQL database and then collects the latest tag list from the SQL database. The PD box also sends a script change check to the SQL and if needed, will update and reboot if there are any new changes to the scripts. The PD box determines from data collected if the closest tag is at the washer PD box. If the tag is closest then it will send a call to the tag to turn on temperature 121.

FIG. 4 describes the Closet process and method of the present invention. In FIG. 4, the Scope Tag or Nurse Tag at the sink, AER, or Room sends RSSI and ID Values over Bluetooth to the PD Box located in the closet. The PD closet box then collects sample RSSI values. It takes the average of these values and with a date stamp, sends them to the PC at that location. Every 45 seconds, the PD box then sends a location check in to the SQL database, and then collects the latest tag list from the SQL database. The PD box also sends a script change check to the SQL database and if needed, will update and reboot if there are any new changes to the scripts. The PD box determines from the data collected if temperature or movement is being collected from the tag 130. If the tag is transmitting temperature and movement it will send a call to the tag to turn off both sensors for temperature and movement 140.

Figure 5:
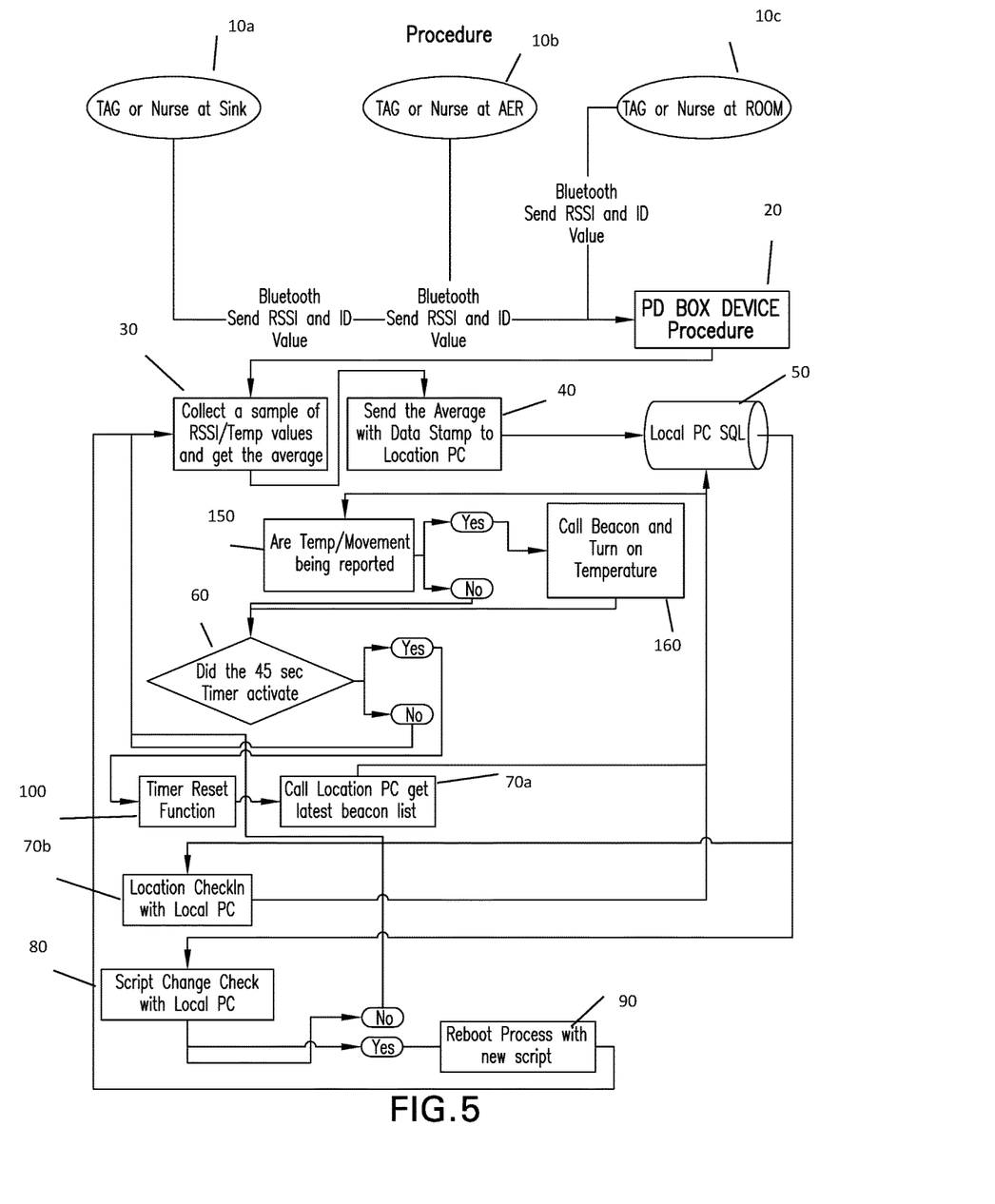
FIG. 5 is a flowchart illustrating is an embodiment of the present system reading the tags in an examination/procedure room.

FIG. 5, similar to FIGS. 2-4, illustrates present system reading the tags in an examination/procedure room. FIG. 5 illustrates the procedure. In FIG. 5, the Scope Tag or Nurse Tag at the sink, AER, or Room sends RSSI and ID Values over Bluetooth to the PD Box located in the procedure room. The PD room box then collects sample RSSI and temperature values. It takes the average of these values and with a date stamp sends them to the PC at that location. The PC, using a SQL database then sends a location check in to the PD Box. Every 45 seconds the PD box then sends a location check in to the SQL Database, and then collects the latest tag list from the SQL database. The PD box also sends a script change check to the SQL database and if needed, will update and reboot if there are any new changes to the scripts. The PD box determines from the data collected whether temperature or movement being reported or collected from the tag 150. If the tag is transmitting temperature and movement, the PD box will send a call to the tag or beacon to turn on the temperature and movement sensors 160.

Figure 6:
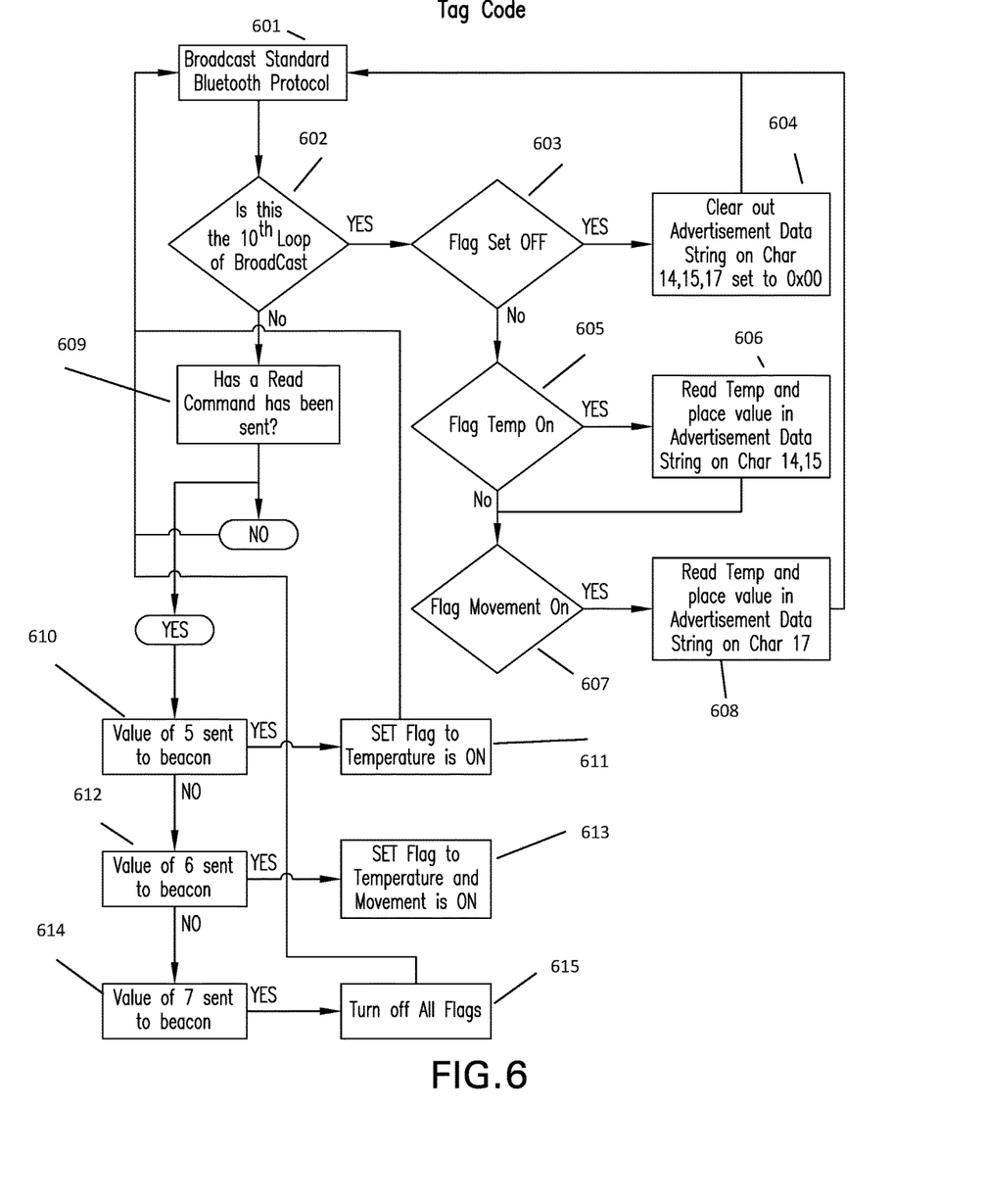
FIG. 6 is a flowchart illustrating processing of a tag or beacon to manage temperature, movement, location, etc. of the medical device.

Referring now to FIG. 6, there is a flowchart illustrating a management of the medical device. The tag and subsequently the medical device preferably uses a Bluetooth® wireless communication protocol. This enables communication with the box and with any other tag of the system. A check may occur to determine how many loops of the broadcast message has occurred. If a read command has been sent, the message is continued to be sent. If a read command has been sent, then the value of the message loop determines what functionality is turned on or off. Each tag may be assigned a specific code thereby identifying the particular medical device or person associated with the tag. The information after being read from the tag may reset the broadcast message.

FIG. 6 further describes the tag code. The tag broadcasts a standard Bluetooth protocol 601. The tag then determines every $10^{th}$ loop of the broadcast 602. If it is the $10^{th}$ loop of the broadcast, the tag will then determine if the flag set is off 603. If the flag is set off, it will then clear out any advertisement data string on characters (herein char) 14, 15, 17 set to 0x00 604 and return to broadcasting standard Bluetooth protocol. Char provides for fixed-length storage of strings and is the length that is an unsigned integer literal designating the length in bytes. The default length for a CHAR is 1, and the maximum size of length is 254. If flag set is on, the tag will check if flag temperature is on 605. If yes, the tag will read temperature and place value in advertisement data string on char 14, 15 606 and then check if flag movement is on. If flag temperature was off, the tag will also check if flag movement is on 607. If flag movement is on 607, the tag will read movement and place the value in advertisement data string on char 17 then return to broadcast standard Bluetooth protocol 608. If off, the tag will also return to broadcasting standard Bluetooth protocol. If while checking if it's the $10^{th}$ loop and it is not, the tag will then check if a read command has been sent 609. If it hasn't, the system will return to broadcasting standard Bluetooth protocol. If it has been sent, a read command it will react according to the command. For a value of 5 (610), the tag will set a flag for temperature on 611. For a value of 6 (612), the tag will set flag temperature and movement on 613. For a value of 7 (614), the tag will turn off all flags 615.

Figure 7:
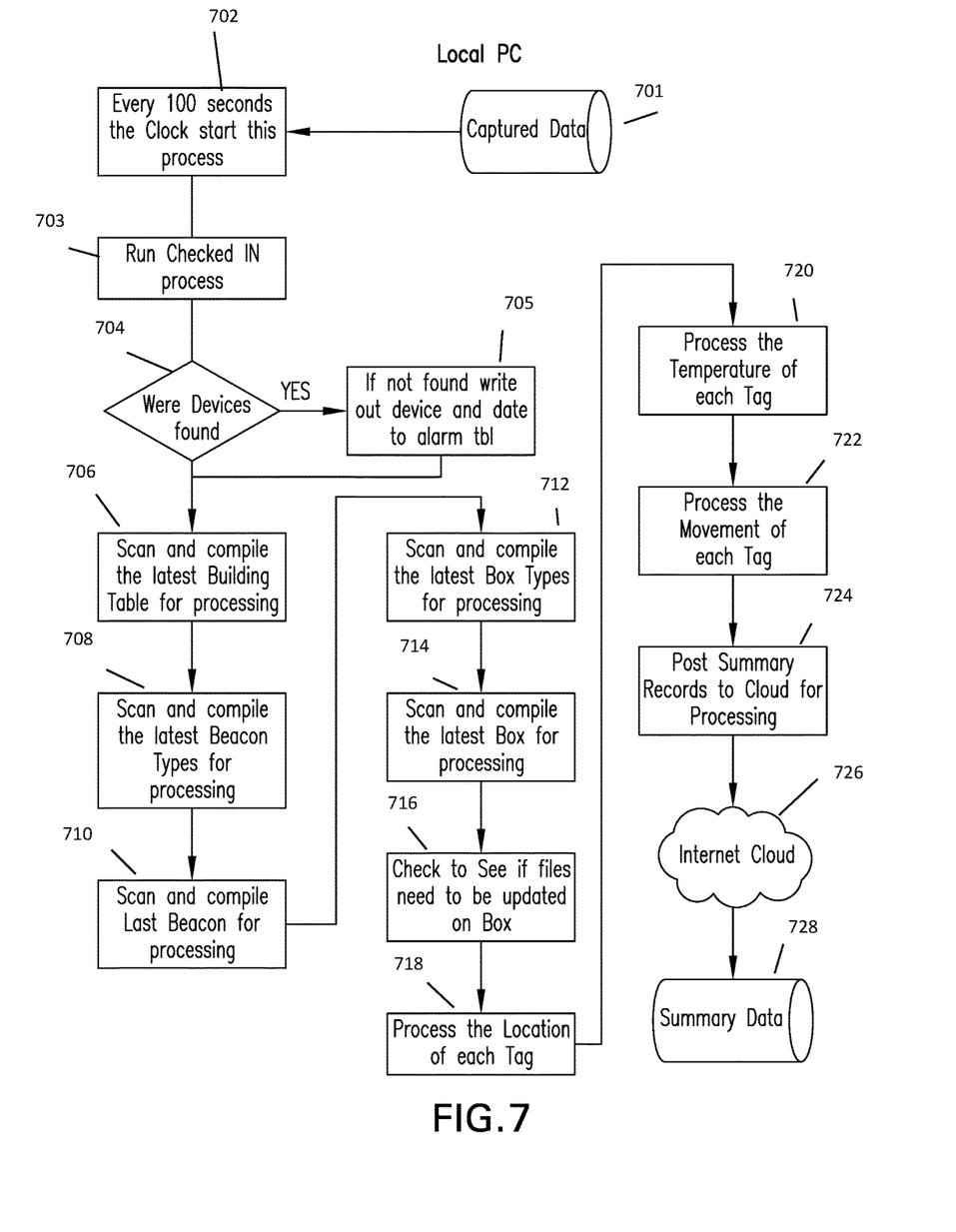
FIG. 7 is a flowchart illustrating a management of collected data and reporting of the data.

In FIG. 7, there is a flowchart illustrating management of the collected data and reporting of said data. Once the data has been captured, a check in process is performed to determine if any "new" devices are found within a tag reading vicinity. The information associated with each tag such as location, movement, and temperature is logged and stored by the system. Such information may be locally stored, stored in the cloud, or a combination thereof. The information allows a complete history of usage, cleaning, and other general maintenance to be ascertained.

In FIG. 7, the local PC process and flow is described. Captured data 701 is processed by the PC every 100 seconds 702. The PC's clock starts this process. The PC runs a checked in process 703. If a device is not found 704, the PC will write out device and date to the alarm table 705. If the device is found 704, the PC will scan and compile latest building table for processing 706. The PC will then scan and compile the latest tag type for processing 708. The PC will then scan and compile the last tag or beacon for processing 710. The PC will then scan and compile the latest box types for processing 712. The PC will then scan and compile the latest box for processing 714. After this, the PC will check to see if files need to be updated on the box 716. Then the PC will process the location of each tag 718. Then in order, the PC will process the temperature 720, then movement 722 and then the PC will post summary records to the cloud for processing 724. The cloud on the Internet 726 then will send out the summary data to be viewed 728.

Figure 8:
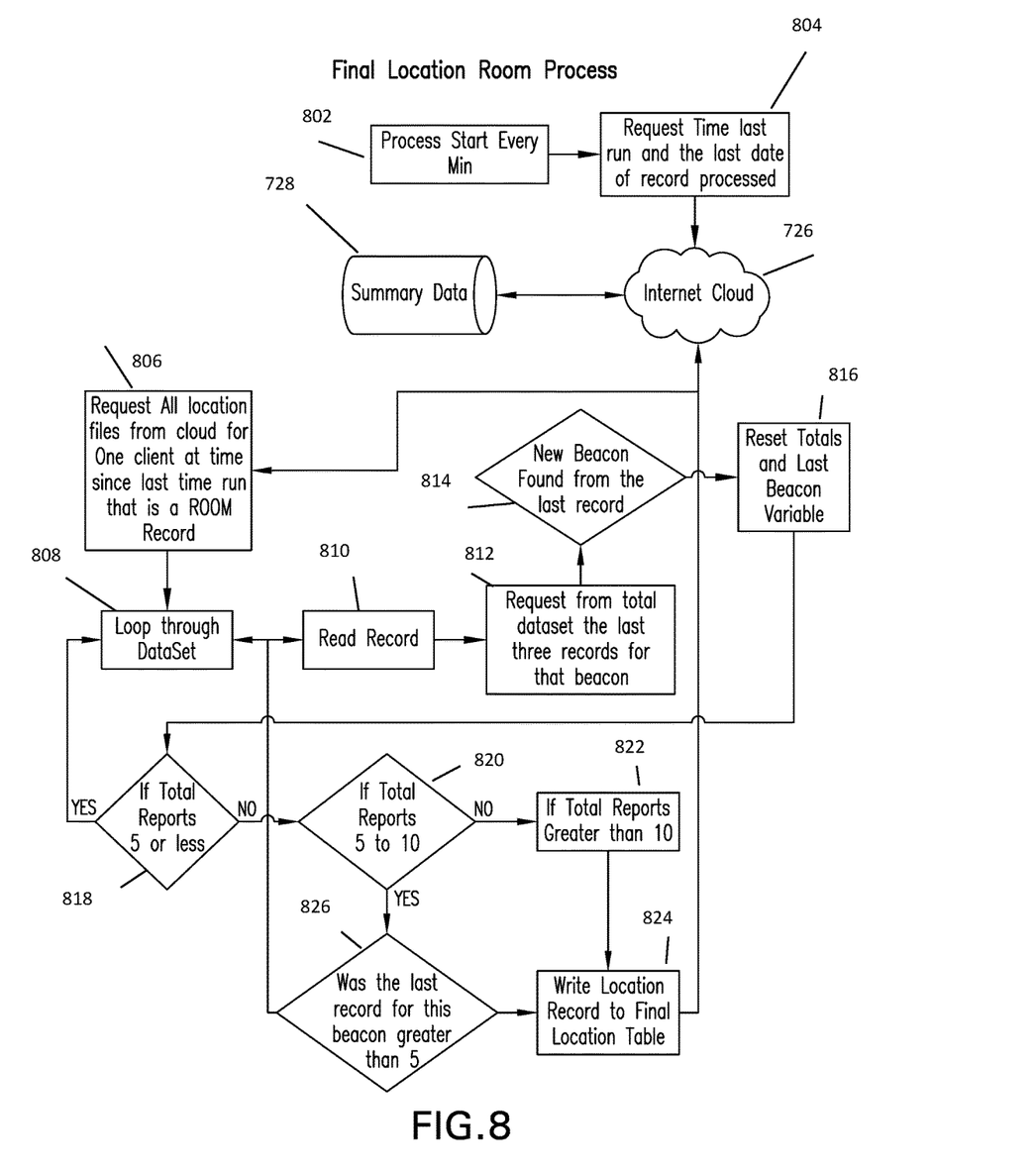
FIG. 8 is a flowchart illustrating a process of finding a location room of the medical device.

FIG. 8 illustrates the process of finding a location room or location of the medical device. About every 5 seconds to about every 5 minutes and more preferably about every 1 minute 802, a message is sent to determine the location of the medical device. This information is preferably stored on both the cloud 726 and the local storage device at the medical facility or setting. The information is captured and stored as needed. In some instances, the data is captured and overwritten to preserve storage space and the data requirements by the system as a whole. The summary data 728 that is sent to the cloud 726 will then start a process every minute 802 that will request time last run and the last date of record processed 804. A request will be sent for all location files from the cloud for "one client at time since last time run that is a room record," 806. The request will loop through a data set 808 and it will read the record 810, and then request from the total dataset the last three records for that beacon or tag 812. If a new beacon and tag is found from the last record, then it resets totals and last tag variable 816. If the total reports are 5 or less 818, then it will loop through again and repeat the steps. If more than 5 reports are found then it will determine if total reports are in 5 to 10 (820). If more than ten reports 822, then the location record will be written to final location table 824 and send to the cloud 726. If the total reports are between 5-10 (820) and the last tag is greater than 5 (826), then it will skip ahead of another loop through the dataset and repeat the process starting at reading the record 810.

Figure 9:
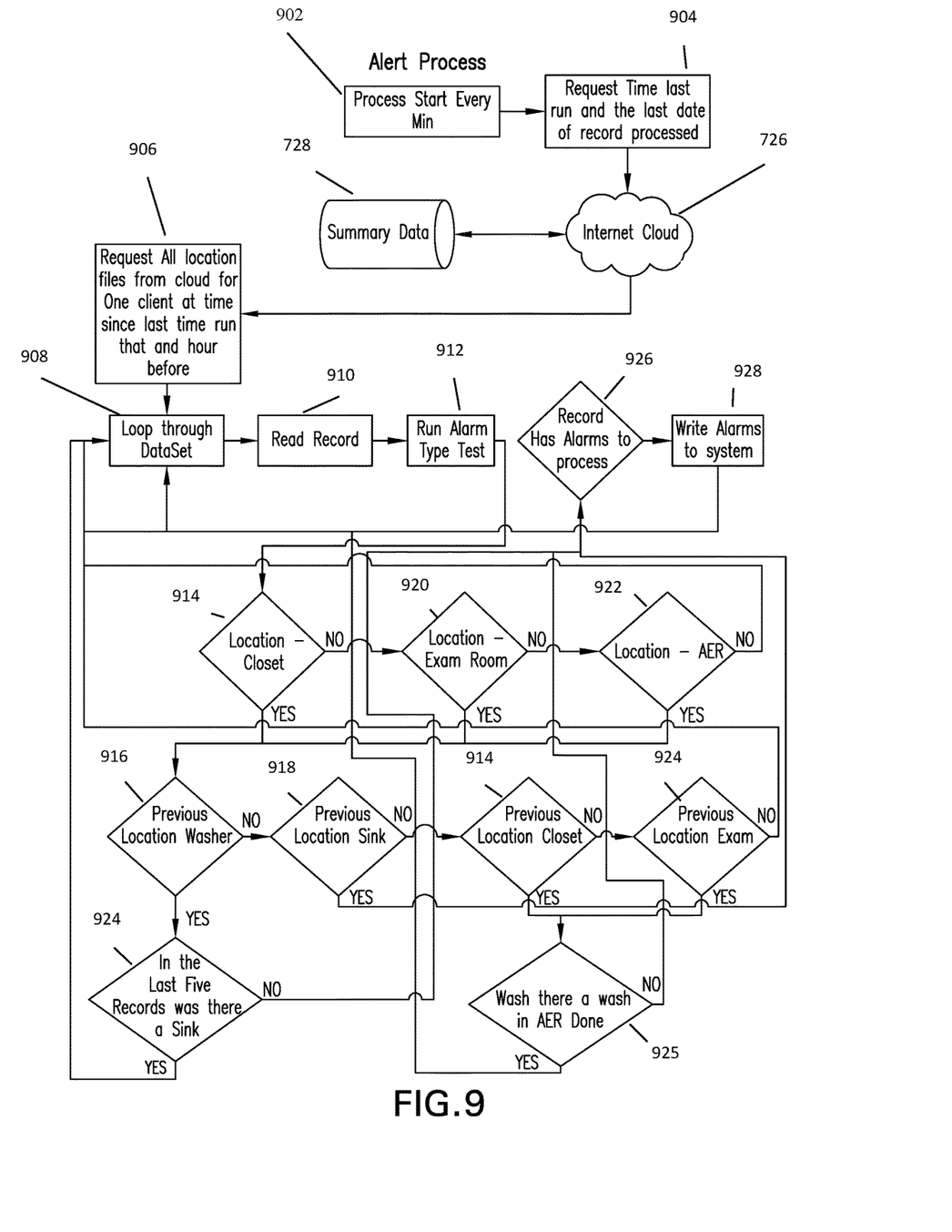
FIG. 9 is a flowchart illustrating a process to report alerts when protocols relating to the medical device are not adhered.

In FIG. 9, alerts can be generated and sent to an electronic device (e.g. smartphone) to alert at least one individual(s) that the proper reprocessing procedure has been performed. The cloud software collects all the data from the medical facility, and preferably filters out any noise and detects the location of each device at each second. The cloud software then creates alerts (e.g. if proper sequence isn't used (sink then washer), if proper temperature isn't used, if proper time isn't spent, if scope repairs are needed or performed (scope beacon can be "checked out" for repairs to scope; repairs can be emergency repairs or routine maintenance—not currently required but expect to be implemented soon) (i.e. alert will be issued if scope is in repair mode).

The alerts may then go to the mobile application which should be used preferably by the system administrator and any maintenance personnel. Alerts can be cleared by the administrator, as can the repair notes; however, all of the historical data will be kept in the cloud, as will any past versions of any edits made on the app. There may also be alerts for system failure of beacons and/or device units on the app. That way the system will be aware that if units have to be swapped out and/or any medical devices have been stolen, etc.

FIG. 9 describes the Alert process in detail. The summary data that is in the cloud will then start a process every minute 902 that will request time last run and the last date of record processed 904. A request will be sent for all location files from the cloud 726 for one client at time since last time run that and hour before 906. It will loop through the data set 908 and it will read the record 910 and then run alarm type test 912. If the location is a closet 914, the system will check if the previous location is a washer 916, sink 918, exam room 920 or AER 922. If according to protocols set by client, the previous location is incorrect it will record alarms to process 926 and write the alarms to the system 928. If the system determines that in the last five records, there was no sink 924 in the process or if the wash did not include a wash done via the AER 925, then the system will record alarms and write alarms into the system process.

Figure 10:
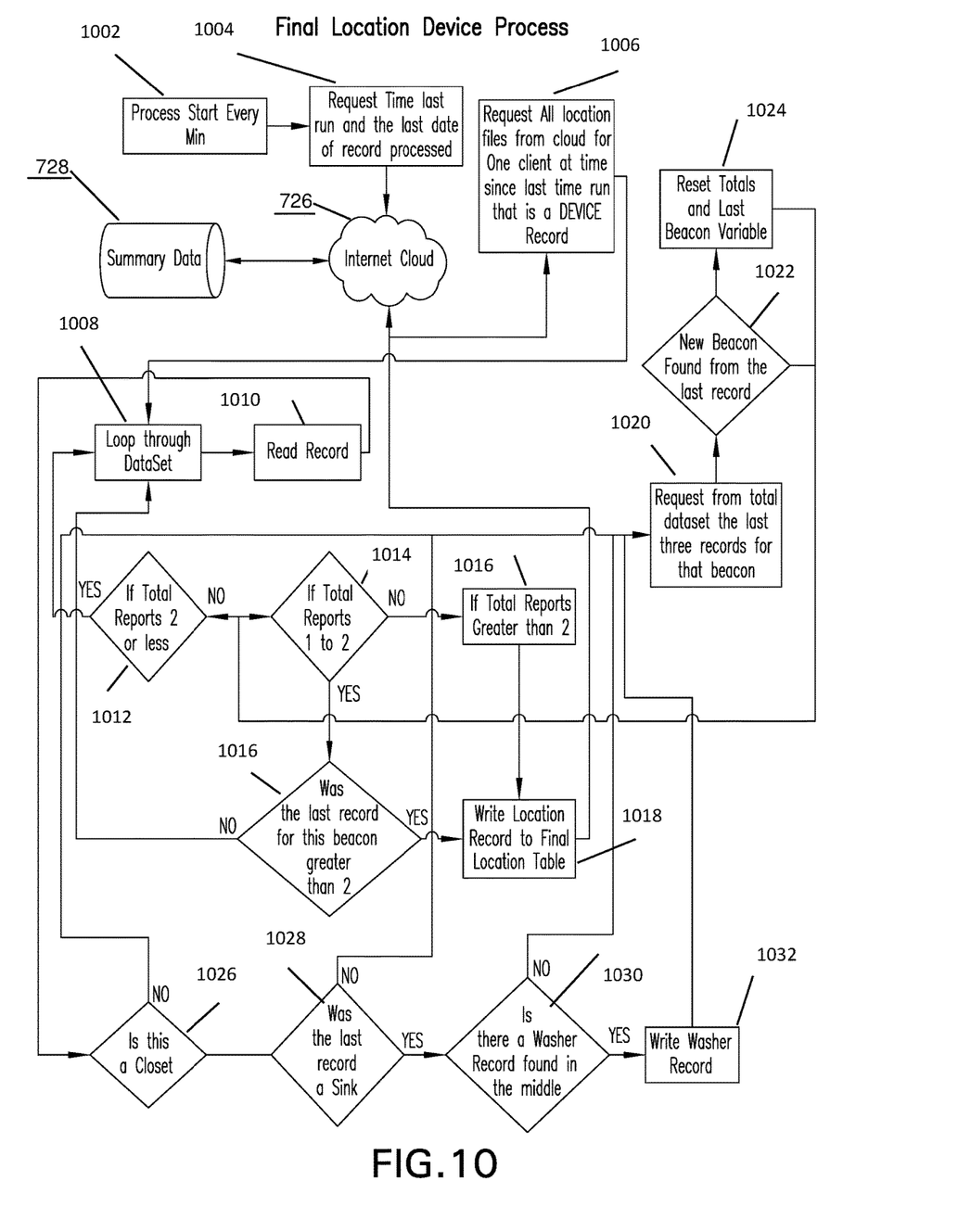
FIG. 10 is a flowchart illustrating another embodiment of a process of finding a location room of the medical device.

FIG. 10 display another embodiment of finding a location of a particular medical device using the present system. FIG. 10 describes the Final location device process procedure. The summary data 728 that is stored in the cloud 726 will then start a process every minute 1002 that will request time last run and the last date of record processed 1004. A request will be sent for all location files from the cloud for one client at time since last time run that is a device record 1006. It will loop through the data set 1008 and it will read the record 1010. If the record states it's a station it will check if the total reports are 2 or less 1012 or 1 or 2 (1014). If yes, it will loop through the data set again. It will keep performing this until the total reports are greater than 2 (1016), then it will write or record the record to the final location table 1018. It will then request from the total the last three records for that tag 1020. If a new tag is found from the last record 1022 it will reset totals and the last tag variable 1024. If when reading the record 1010, the system determines that the tag is located in a closet 1026, and that the last record contained a sink 1028, and that there is a washer record found in the middle of the location 1030 then the washer record will be recorded 1032.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A medical device cleaning and tracking system comprising:
a processor having a memory, the memory having computer readable instructions stored thereon that when executed by the processor, enable monitoring of at least one medical device having a first tag, wherein the first tag is configured to measure at least location, movement, and temperature of the at least one medical device;
a second tag operably coupled to the processor, the second tag being configured to monitor the at least one medical device, wherein the second tag is configured to communicate with the first tag and receive information pertaining to the at least one medical device therefrom; and, wherein the memory further comprises instructions, that when executed by the processor, issues an alarm in response to failure to detect a proper temperature.

2. The system of claim 1 further comprising at least one additional tag configured to monitor the at least one medical device.

3. The system of claim 1 wherein the at least one medical device is an endoscope.

4. The system of claim 1, wherein the memory further comprises instructions, that when executed by the processor, cause the processor to perform the steps of:
recording a location history for the at least one medical device; and
issuing an alarm in response to determining an absence of a sink record within a predetermined number of previous locations within the recorded location history.

5. The system of claim 1, wherein the memory further comprises instructions, that when executed by the processor, cause the processor to perform the steps of:
detecting a distance between the at least one medical device and a sink;
activating additional broadcast data from the at least one device when the detected distance is below a predetermined threshold.

6. The system of claim 1, wherein the memory further comprises instructions, that when executed by the processor, cause the processor to perform the steps of:
detecting a distance between the at least one medical device and a sink;
deactivating additional broadcast data from the at least one device when the detected distance is below a predetermined threshold.

7. A method of tracking a medical device, the method comprising the steps of:
monitoring, via a processor, a location of at least one medical device;
monitoring, via the processor, a temperature of the at least one medical device;
monitoring, via the processor, a movement of the at least one medical device;
logging, via the processor, the location, the temperature, and the movement of the at least one medical device;
storing, on a computer readable memory operably coupled to the processor, the location, the temperature, and the movement of at least one medical device;

wherein if a location, temperature, or movement of the at least one medical device meets a predetermined threshold, then no alert is generated; and wherein if a location, temperature, or movement of the at least one medical device does not meet a predetermined threshold, then an alert is sent to at least one electronic device.

8. The method of claim 7, further comprising at least one additional tag configured to monitor the at least one medical device.

9. The method of claim 7, wherein the at least one medical device is an endoscope.

10. The method of claim 7, further comprising:
recording a location history for the at least one medical device; and
issuing an alarm in response to determining an absence of a sink record within a predetermined number of previous locations within the recorded location history.

11. The method of claim 10, wherein the predetermined number of previous locations within the recorded location history is five.

12. The method of claim 7, further comprising:
detecting a distance between the at least one medical device and a sink; and
activating additional broadcast data from the at least one device when the detected distance is below a predetermined threshold.

13. The method of claim 12, wherein the additional broadcast data includes temperature data.

14. The method of claim 7, further comprising:
detecting a distance between the at least one medical device and a sink;
deactivating additional broadcast data from the at least one device when the detected distance is below a predetermined threshold.

15. The method of claim 14, wherein the additional broadcast data includes motion data.

* * * * *